(12) United States Patent
Yao et al.

(10) Patent No.: US 11,771,325 B2
(45) Date of Patent: *Oct. 3, 2023

(54) MULTISPECTRAL SYNCHRONIZED IMAGING

(71) Applicant: SYNAPTIVE MEDICAL INC., Toronto (CA)

(72) Inventors: Ze Shan Yao, Toronto (CA); Piotr Kuchnio, Toronto (CA); Michael Frank Gunter Wood, Toronto (CA); Tammy Kee-Wai Lee, Toronto (CA); Yanhui Bai, Toronto (CA); Michael Peter Bulk, Toronto (CA); Christopher Thomas Jamieson, Toronto (CA)

(73) Assignee: Synaptive Medical Inc.

( * ) Notice: Subject to any disclaimer, the term of this patent is extended or adjusted under 35 U.S.C. 154(b) by 226 days.

This patent is subject to a terminal disclaimer.

(21) Appl. No.: 17/301,997

(22) Filed: Apr. 21, 2021

(65) Prior Publication Data

US 2021/0235991 A1 Aug. 5, 2021

Related U.S. Application Data

(63) Continuation of application No. 15/504,057, filed as application No. PCT/IB2016/052678 on May 10, 2016, now Pat. No. 11,013,414.

(51) Int. Cl.
*A61B 5/00* (2006.01)
*A61B 34/20* (2016.01)
(Continued)

(52) U.S. Cl.
CPC .......... *A61B 5/0075* (2013.01); *A61B 5/0042* (2013.01); *A61B 5/0071* (2013.01);
(Continued)

(58) Field of Classification Search
None
See application file for complete search history.

(56) References Cited

U.S. PATENT DOCUMENTS

| 5,400,791 A | 3/1995 | Schlier |
| 5,910,816 A | 6/1999 | Fontenot |
| 2012/0130258 A1 | 5/2012 | Taylor |

OTHER PUBLICATIONS

Examination report issued by the Intellectual Property Office of the UK in relation to GB Application No. GB1820036.0 dated Apr. 14, 2021, 3 pgs.

*Primary Examiner* — Colin T. Sakamoto

(57) ABSTRACT

A multispectral synchronized imaging system is provided. A multispectral light source of the system comprises: blue, green and red LEDs, and one or more non-visible light sources, each being independently addressable and configured to emit, in a sequence: at least visible white light, and non-visible light in one or more given non-visible frequency ranges. The system further comprises a camera and an optical filter arranged to filter light received at the camera, by: transmitting visible light from the LEDs; filter out non-visible light from the non-visible light sources; and otherwise transmit excited light emitted by a tissue sample excited by non-visible light. Images acquired by the camera are output to a display device. A control unit synchronizes acquisition of respective images at the camera for each of blue light, green light, visible white light, and excited light received at the camera, as reflected by the tissue sample.

21 Claims, 12 Drawing Sheets

(51) Int. Cl.
*A61B 5/026* (2006.01)
*G01J 3/443* (2006.01)
*A61B 90/00* (2016.01)
*A61B 5/06* (2006.01)
*G01J 3/28* (2006.01)
*G01J 3/10* (2006.01)
*G01J 3/02* (2006.01)
*A61B 90/20* (2016.01)
*A61B 90/30* (2016.01)
*A61B 17/34* (2006.01)

(52) U.S. Cl.
CPC .......... *A61B 5/0077* (2013.01); *A61B 5/0082* (2013.01); *A61B 5/0084* (2013.01); *A61B 5/026* (2013.01); *A61B 5/061* (2013.01); *A61B 5/748* (2013.01); *A61B 5/7425* (2013.01); *A61B 34/20* (2016.02); *A61B 90/361* (2016.02); *G01J 3/0248* (2013.01); *G01J 3/10* (2013.01); *G01J 3/2803* (2013.01); *G01J 3/2823* (2013.01); *G01J 3/443* (2013.01); *A61B 5/0261* (2013.01); *A61B 5/725* (2013.01); *A61B 17/34* (2013.01); *A61B 90/20* (2016.02); *A61B 2034/2055* (2016.02); *A61B 2090/309* (2016.02); *A61B 2562/0233* (2013.01); *A61B 2562/0242* (2013.01); *G01J 2003/106* (2013.01); *G01J 2003/2826* (2013.01)

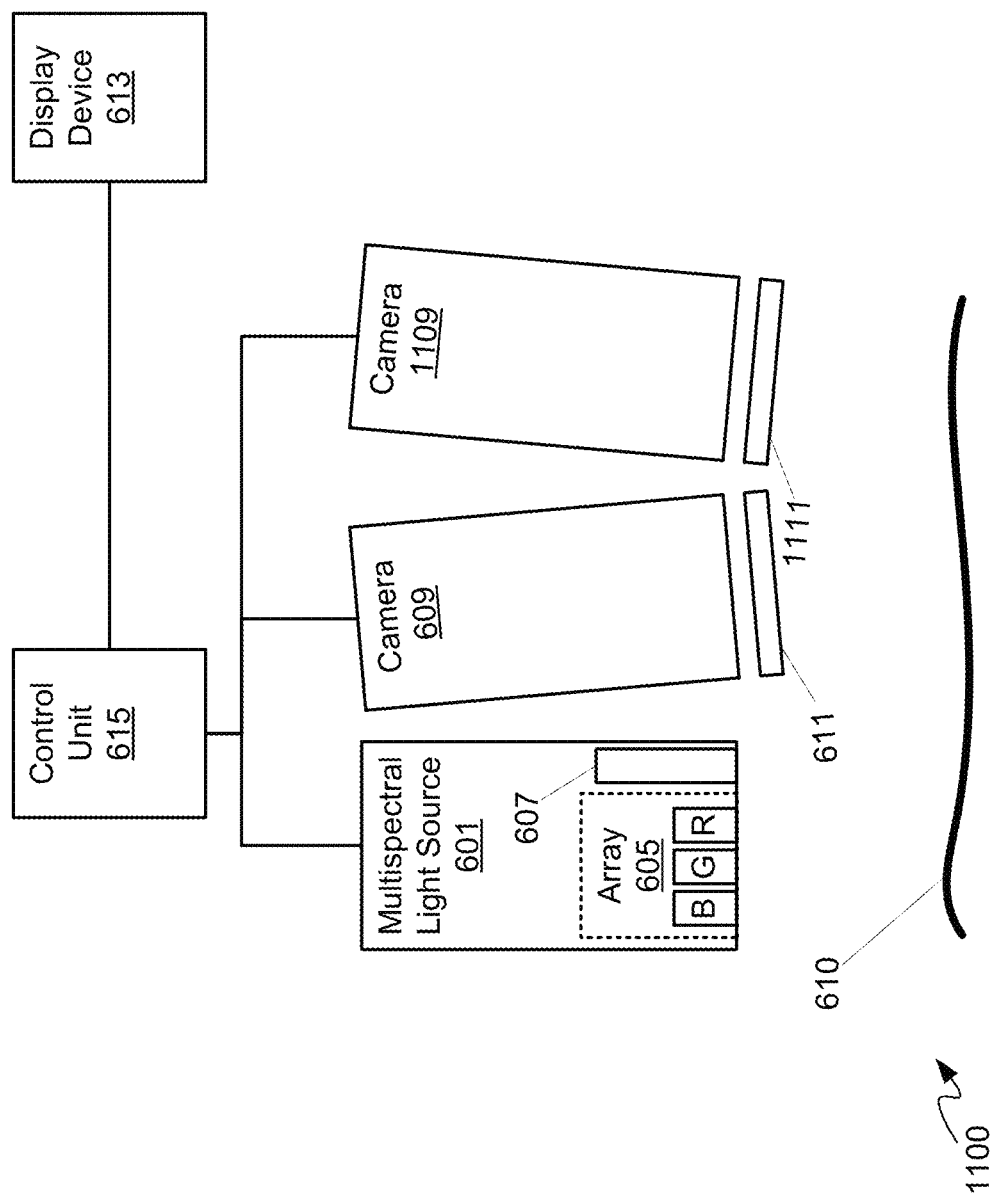

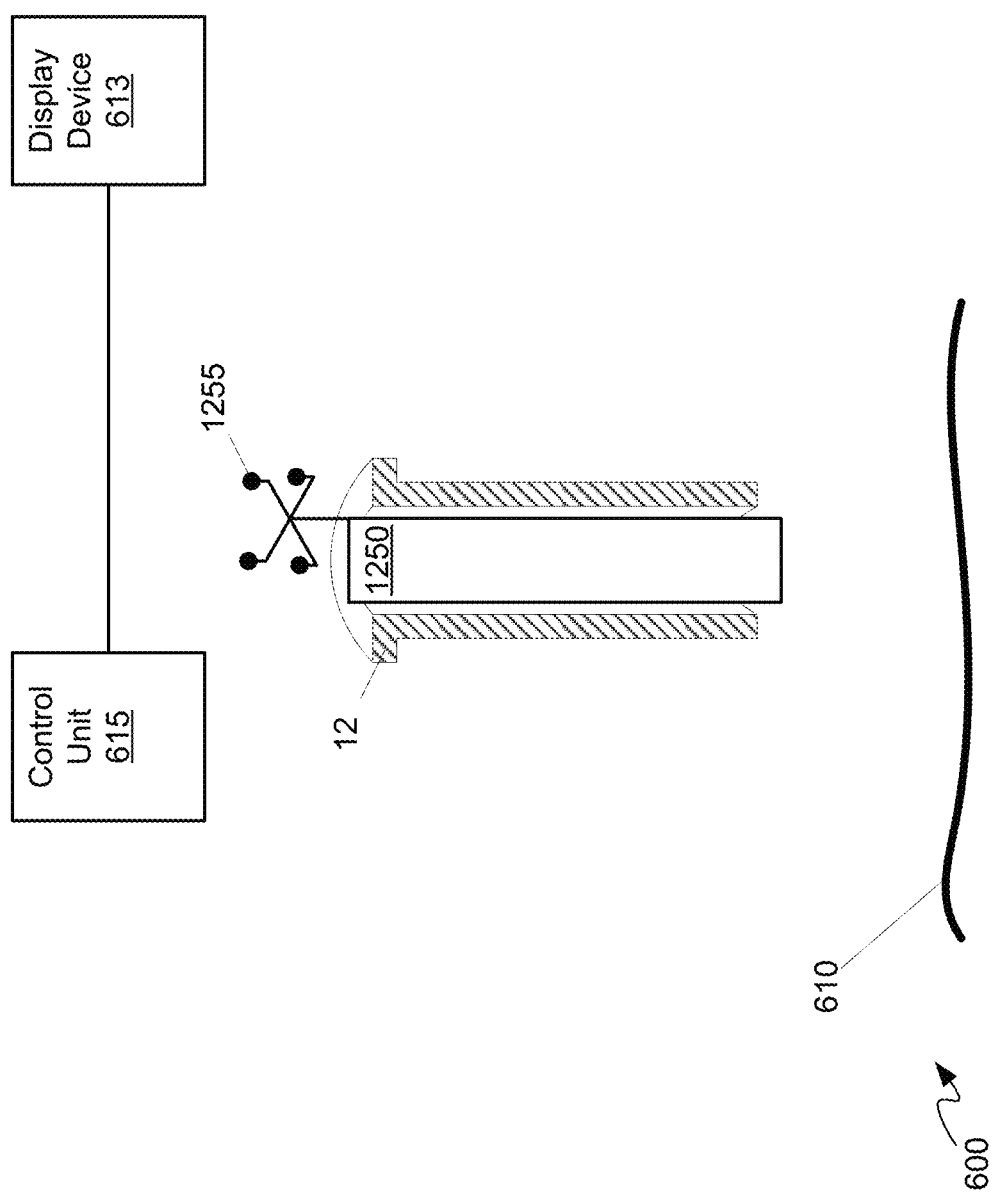

MULTISPECTRAL SYNCHRONIZED IMAGING

CROSS-REFERENCE TO RELATED APPLICATION(S)

This document is a continuation application which claims the benefit of, and priority to: U.S. patent application Ser. No. 15/504,057, filed on Feb. 15, 2017, entitled "MULTISPECTRAL SYNCHORNIZED IMAGING" and International Patent Application No. PCT/IB2016/052678, filed on May 10, 2016, entitled "MULTISPECTRAL SYNCHORNIZED IMAGING," all of which are incorporated herein by reference in their entirety.

FIELD

The present disclosure generally relates to medical imaging and methods for minimally invasive therapy and image-guided medical procedures and specifically relates to a system and method of multispectral synchronized imaging.

BACKGROUND

Image-guided medical procedures include fluorescence-guided surgery (FGS), a medical imaging technique that is used to facilitate the delineation of the tumor margin during surgery or vascular angiography. With the current mainstream technology, changing from normal white light surgery (WLS) to FGS requires a mechanical filter wheel for switching of the emission filter on a camera side and another filter wheel on an illumination side to constrict the wavelength to an optimal narrow band. This mechanical switching creates a significant delay which restricts the possibility of concurrent imaging of WLS and FGS. In addition, Indocyanine green (ICG) fluorescent dye, used in FGS, has an emission spectrum (820 nm-860 nm) that can overlap with infrared tracking pulses that are used in intermittent tracking of surgical tools, thereby creating an artifact on an acquired image, and thereby restricting a concurrent tracking mode and ICG-FGS during surgery.

SUMMARY

The present disclosure is generally directed to image-guided medical procedures using an access port. This port-based surgery approach allows a surgeon, or robotic surgical system, to perform a surgical procedure, involving tumor resection in which the residual tumor is minimized, while also minimizing trauma to intact white matter and grey matter of the brain. In such procedures, trauma may occur, for example, due to contact with the access port, stress to the brain matter, unintentional impact with surgical devices, and/or accidental resection of healthy tissue.

Hence, an aspect of the present disclosure provides a multispectral synchronized imaging system comprising: a multispectral light source comprising: a light emitting diode (LED) array comprising: at least one blue LED, at least one green LED and at least one red LED; and one or more non-visible light sources arranged side by side with the LED array, each of the at least one blue LED, the at least one green LED, the at least one red LED, and the one or more non-visible light sources being independently addressable such that the multispectral light source is configured to emit in a sequence: at least visible white light, and non-visible light in one or more given non-visible frequency ranges; a camera arranged to receive light from a tissue sample illuminated by the multispectral light source in the sequence; an optical filter arranged to filter the light from the tissue sample received at the camera, the optical filter configured to: transmit visible light from the LED array; filter out non-visible light from the one or more non-visible light sources in the one or more given non-visible frequency ranges; and otherwise transmit excited light emitted by the tissue sample under excitation by the non-visible light from the one or more non-visible light sources; a display device; and, at least one control unit configured to: control the multispectral light source to emit the sequence; synchronize acquisition of respective images at the camera for each of blue light, green light, the visible white light, and the excited light received at the camera, as reflected by the tissue sample; and, output the respective images in a respective sequence to the display device.

The one or more non-visible light sources comprise an ultraviolet (UV) LED; and the optical filter is configured to: filter out UV light from the UV LED; and transmit the excited light emitted by the tissue sample under excitation from the UV LED. The one or more non-visible light sources comprise an ultraviolet (UV) light source and an infrared (IR) light source; and the optical filter is configured to: transmit light in a fluorescent range of approximately 430 nm to approximately 700 nm, and from approximately 820 nm to approximately 860 nm to allow light from emission of one or more of Protoporphyrin IX (PpIX) and ICG at the tissue sample to be imaged by the camera; and block light from both the UV light source and the IR light source from entering the camera. The one or more non-visible light sources can comprise an infrared (IR) laser, and the optical filter is configured to: filter out IR light from the IR laser; and transmit the excited light emitted by the tissue sample under excitation from the IR laser.

The one or more non-visible light sources comprise an infrared (IR) laser; and the system further comprises a second optical filter, exchangeable for the optical filter under control by the at least one control unit. The second optical filter is configured to transmit light from the IR laser. The IR laser is operable in one of a diffused mode, when the optical filter is filtering light to the camera, and a speckled mode when the second optical filter is filtering light to the camera. The IR laser is operable in a speckled mode when the second optical filter is filtering light to the camera; and the sequence comprises green light emitted from the green LED, and blue light emitted from the blue LED, when the optical filter is filtering light to the camera, and speckled laser light from the IR laser in the speckled mode, the green light and the blue light used for functional imaging of blood flow in the tissue sample.

The sequence comprises alternating the visible white light and the non-visible light. The sequence can comprise alternating the visible white light, green light, blue light, and the non-visible light. The sequence can comprise: one or more of a user-configured sequence; and simultaneous emission of light from two or more of the at least one blue LED, the at least one green LED, the at least one red LED. Respective relative intensity of each of the at least one blue LED, the at least one green LED, the at least one red LED is adjusted to change one or more of: color temperature of the visible white light; and color rendering of the respective images at the display device.

The multispectral synchronized imaging system further comprises: a second camera arranged relative to the camera to acquire three-dimensional images of the tissue sample: and a second optical filter is configured to: transmit visible light from the LED array and transmit non-visible light from the one or more non-visible light sources in the one or more given non-visible frequency ranges. The one or more non-visible light sources comprise an IR laser operable in one of a diffused mode and a speckled mode. The camera and the second camera is configured to capture images independent of one another. Image capture times of each the camera and the second camera are off-set with respect to one another.

The at least one control unit is further configured to output the respective images in the respective sequence to the display device at a rate, wherein the respective images appear simultaneously rendered to a human vision system. The camera comprises an optical camera. The multispectral synchronized imaging system further comprises a thermal camera arranged to receive the light from the tissue sample illuminated by the multispectral light source in the sequence. The at least one control unit can comprise one or more ports configured to communicate with one or more of: external computing devices; electronic surgical devices; trackers; and infrared trackers. The camera and the optical filter are configured for use with a surgical port, the surgical port configured for corridor-based surgery.

BRIEF DESCRIPTION OF THE DRAWINGS

For a better understanding of the various implementations herein described and to show more clearly how they may be carried into effect, reference will now be made, by way of example only, to the accompanying drawings in which:

FIG. 11 is a diagram illustrating a multispectral synchronized imaging system adapted for use with two cameras, according to non-limiting implementations; and FIG. 12 is a diagram illustrating a multispectral synchronized imaging system adapted for use with an access port for corridor based surgery, according to non-limiting implementations.

DETAILED DESCRIPTION

Various implementations and aspects of the present disclosure will be described with reference to details below discussed. The following description and drawings are illustrative of the present disclosure and are not to be construed as limiting the present disclosure. Numerous specific details are described to provide a thorough understanding of various implementations of the present disclosure. However, in certain instances, well-known or conventional details are not described in order to provide a concise discussion of implementations of the present disclosure.

The systems and methods herein described are useful in the field of neurosurgery, including oncological care, neurodegenerative disease, stroke, brain trauma, and orthopedic surgery; however, appreciates is the ability to extend these concepts to other conditions or fields of medicine. Noted is that the surgical process is applicable to surgical procedures for brain, spine, knee, and any other suitable region of the body.

Various apparatuses and processes will be below described to provide examples of implementations of the system disclosed herein. No implementation below described limits any claimed implementation and any claimed implementations may cover processes or apparatuses that differ from those below described. The claimed implementations are not limited to apparatuses or processes having all of the features of any one apparatus or process below described or to features common to multiple or all of the apparatuses or processes below described. Possible is that an apparatus or process below described is not an implementation of any claimed subject matter.

Furthermore, numerous specific details are set forth in order to provide a thorough understanding of the implementations herein described. However, understood is that the implementations herein described are practiced without these specific details. In other instances, well-known methods, procedures, and components have not been described in detail so as not to obscure the implementations herein described.

In this present disclosure, elements are described as "configured to" perform one or more functions or "configured for" such functions. In general, an element that is configured to perform, or configured for performing, a function is enabled to perform the function, is suitable for performing the function, is adapted to perform the function, is operable to perform the function, or is otherwise capable of performing the function.

Understood is that, for the purpose of the present disclosure, the language of "at least one of X, Y, and Z" and "one or more of X, Y, and Z" are construed as X only, Y only, Z only, or any combination of two or more items X, Y, and Z, e.g., XYZ, XY, YZ, ZZ, and the like. Similar logic is applied for two or more items in any occurrence of "at least one . . . " and "one or more . . . " language.

Figure 1:
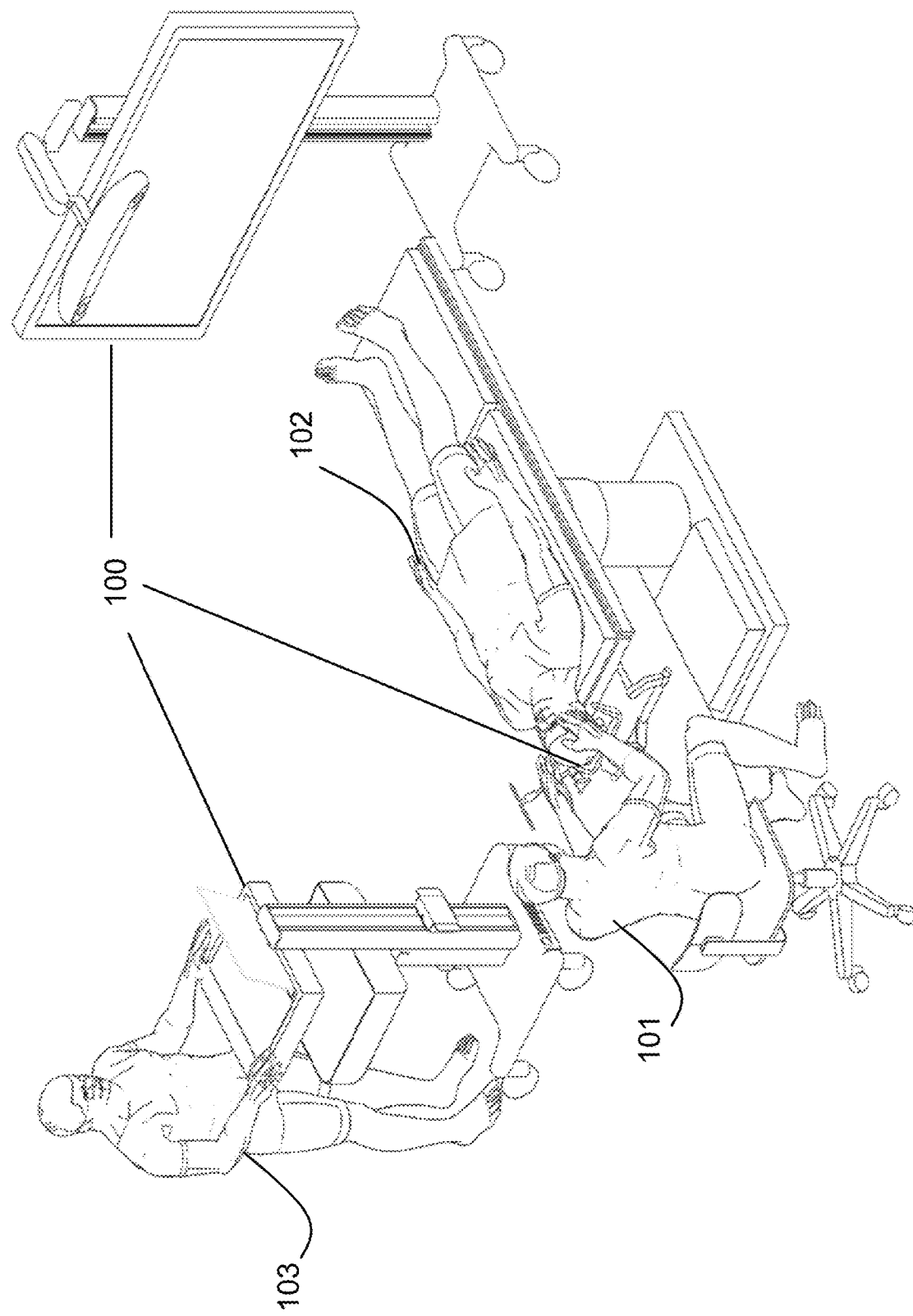
FIG. 1 is a diagram illustrating an example operating room setup for a minimally invasive access port-based medical procedure, according to non-limiting implementations.

Referring to FIG. 1, this diagram illustrates an example navigation system 100 is shown to support minimally invasive access port-based surgery, according to non-limiting implementations of the present disclosure. A neurosurgeon 101 conducts a minimally invasive port-based surgery on a patient 102 in an operating room (OR) environment. The navigation system 100 comprises an equipment tower, tracking system, displays, and tracked instruments to assist the surgeon 101 during the procedure. An operator 103 may also be present to operate, control, and provide assistance for the navigation system 100.

Figure 2:
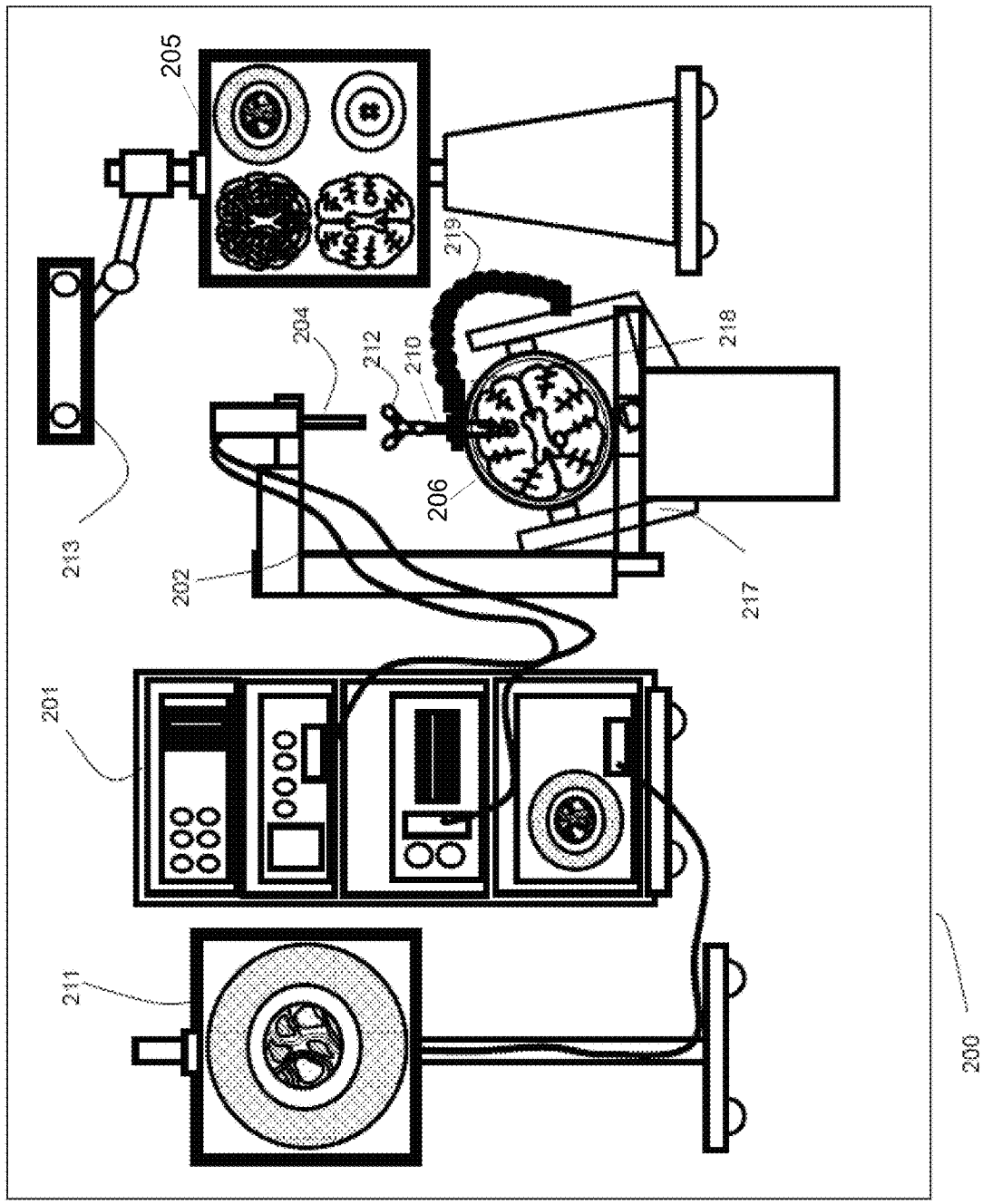
FIG. 2 is a block diagram illustrating components of a medical navigation system that may be used to implement a surgical plan for a minimally invasive surgical procedure, according to non-limiting implementations.

Referring to FIG. 2, this block diagram illustrates components of an example medical navigation system 200, according to non-limiting implementations of the present disclosure. The medical navigation system 200 is shown in a context, wherein a surgical plan, involving equipment, e.g., tool and material, tracking, such as that herein described, is implemented. The medical navigation system 200 comprises one or more monitors 205, 211 for displaying a video image, an equipment tower 201, and a mechanical arm 202, which supports an optical scope 204. The equipment tower 201 is mounted on a frame, e.g., a rack or cart, and contains a computer or controller (examples provided with reference to FIGS. 3 and 6), planning software, navigation software, a power supply, and software to manage the mechanical arm 202, and tracked instruments. In one example non-limiting implementation, the equipment tower 201 comprises a single tower configuration with dual display monitors 211, 205; however, other configurations are also used, e.g., dual tower, single display, etc. Furthermore, the equipment tower 201 is also be configured with a universal power supply (UPS) to provide for emergency power in addition to a regular AC adapter power supply.

Still referring to FIG. 2, a patient's anatomy is held in place by a holder. For example, in a neurosurgical procedure the patient's head is held in place by a head holder 217; and an access port 206 and an introducer 210 is inserted into the patient's head. The introducer 210 is tracked using a tracking camera 213, which provides position information for the navigation system 200. The tracking camera 213 is also be used to track tools and/or materials used in the surgery, as below described in more detail. In one example non-limiting implementation, the tracking camera 213 comprises a 3D (three-dimensional) optical tracking stereo camera, similar to one made by Northern Digital® Imaging (NDI), configured to locate reflective sphere tracking markers 212 in 3D space. In another example, the tracking camera 213 comprises a magnetic camera, such as a field transmitter, wherein receiver coils are used to locate objects in 3D space. Location data of the mechanical arm 202 and access port 206 are determined by the tracking camera 213 detecting the tracking markers 212 placed on these tools, e.g., the introducer 210 and associated pointing tools. Tracking markers are also placed on surgical tools or materials to be tracked. The secondary display 205 provides output of the tracking camera 213. In one example non-limiting implementation, the output is shown in axial, sagittal, and coronal views as part of a multi-view display.

Still referring to FIG. 2, the introducer 210 comprises tracking markers 212 for tracking. The tracking markers 212 comprises reflective spheres in the case of an optical tracking system and/or pick-up coils in the case of an electromagnetic tracking system. The tracking markers 212 are detected by the tracking camera 213; and their respective positions are inferred by the tracking software.

Still referring to FIG. 2, a guide clamp 218 (or more generally a guide) for holding the access port 206 is provided. The guide clamp 218 optionally engages and disengages with the access port 206 without needing to remove the access port 206 from the patient. In some examples, the access port 206 is moveable relative to the guide clamp 218 while disposed in the guide clamp 218. For example, the access port 206 is able to slide up and down, e.g., along the longitudinal axis of the access port 206, relative to the guide clamp 218 while the guide clamp 218 is in a closed position. A locking mechanism is attached to, or integrated with, the guide clamp 218, and is optionally actuatable with one hand, as below further described. Furthermore, an articulated arm 219 is provided to hold the guide clamp 218. The articulated arm 219 comprises up to six degrees of freedom to position the guide clamp 218. The articulated arm 219 is lockable to fix its position and orientation once a desired position is achieved. The articulated arm 219 is attached, or attachable to, a point based on the patient head holder 217, or another suitable point, e.g., on another patient support, such as on the surgical bed, to ensure that, when locked in place, the guide clamp 218 does not move relative to the patient's head.

Figure 3:
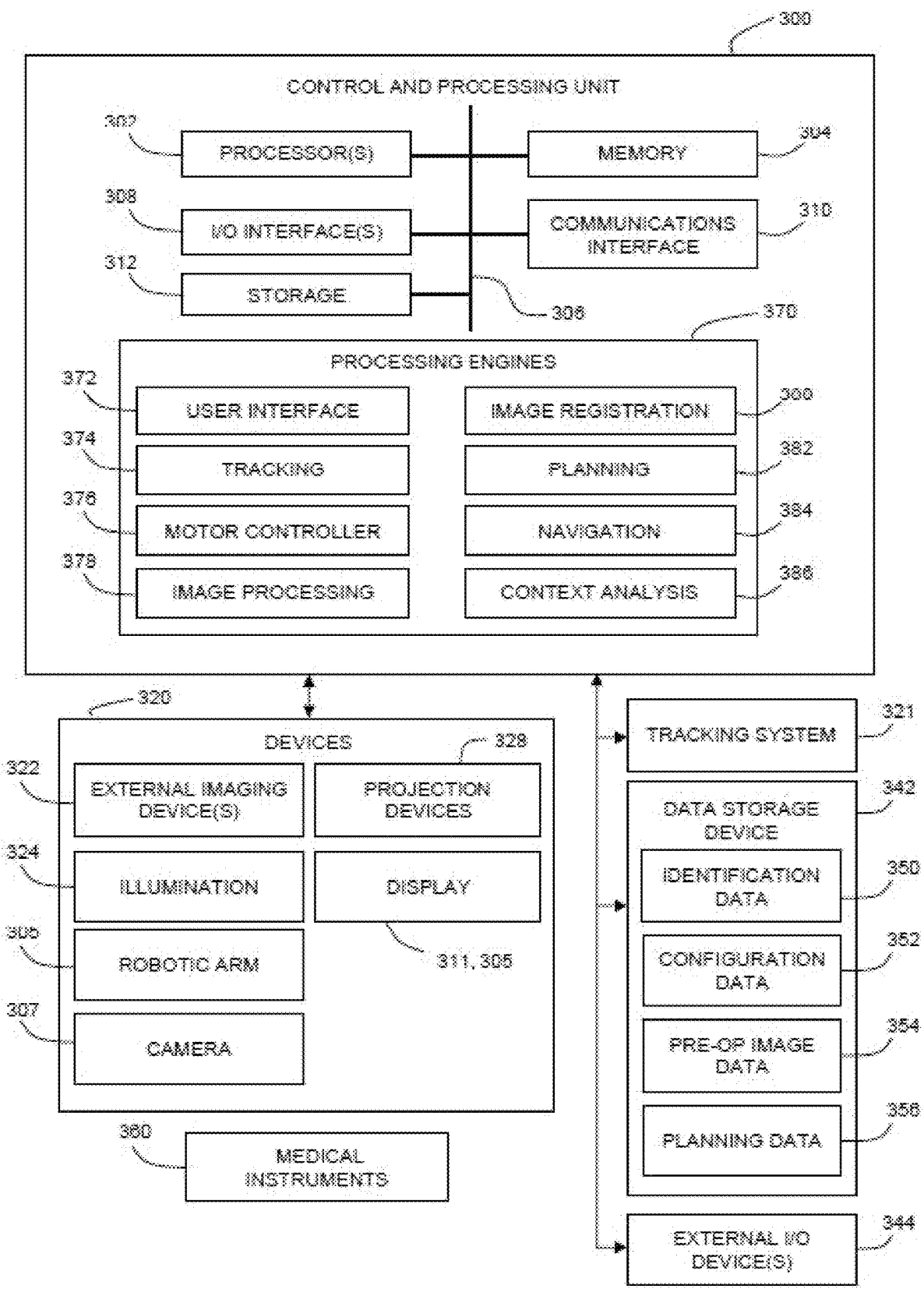
FIG. 3 is a diagram illustrating a block diagram illustrating components of a planning system used to plan a medical procedure implementable using the navigation system, as shown in FIG. 2, according to non-limiting implementations.

Referring to FIG. 3, this block diagram illustrates a control and processing unit 300 usable in the navigation system 200, as shown in FIG. 2, e.g., as part of the equipment tower, according to non-limiting implementations of the present disclosure. In one example non-limiting implementation, the control and processing unit 300 comprises one or more processors 302, a memory 304, a system bus 306, one or more input/output interfaces 308, a communications interface 310, and a storage device 312. In particular, the one or more processors 302 comprise one or more hardware processors and/or one or more microprocessors. The control and processing unit 300 is interfaced with other external devices, such as a tracking system 321, a data storage device 342, and external user input and output devices 344, which comprise one or more of a display, a keyboard, a mouse, a foot pedal, a microphone, and a speaker. Data storage device 342 comprises any suitable data storage device, including, but not limited to, a local and/or remote computing device, e.g. a computer, a hard drive, a digital media device, and/or a server. having a database thereon stored. The data storage device 342 comprises identification data 350 for identifying one or more medical instruments 360 and configuration data 352 that associates customized configuration parameters with one or more medical instruments 360. The data storage device 342 comprises preoperative image data 354 and/or medical procedure planning data 356. Although the data storage device 342 is shown as a single device, in other implementations, the data storage device 342 comprises multiple storage devices.

Still referring to FIG. 3, the medical instruments 360 are identifiable using the control and processing unit 300. The medical instruments 360 are connected to, and controlled by, the control and processing unit 300 and/or the medical instruments 360 being operated and/or otherwise employed, independent of the control and processing unit 300. The tracking system 321 is employed to track the one or more of medical instruments 360 and to spatially register the one or more tracked medical instruments 360 to an intraoperative reference frame. In another example, a sheath is placed over a medical instrument 360; and the sheath is connected to, and controlled by, the control and processing unit 300.

Still referring to FIG. 3, the control and processing unit 300 may also interface with a number of configurable devices, and may intraoperatively reconfigure one or more of such devices based on configuration parameters obtained from the configuration data 352. Examples of devices 320 include, but are not limited, one or more external imaging devices 322, one or more illumination devices 324, a robotic arm, one or more projection devices 328, and one or more displays 305, 311.

Still referring to FIG. 3, aspects of the present disclosure are implemented via the processor(s) 302 and/or the memory 304. For example, the functionalities, herein described, are partially implemented, via hardware logic in the processor 302 and partially implemented using the instructions stored in the memory 304, as one or more processing modules 370 and/or processing engines. Example processing modules include, but are not limited to, user interface engine 372, a tracking module 374, a motor controller 376, an image processing engine 378, an image registration engine 380, a procedure planning engine 382, a navigation engine 384, and a context analysis module 386. While the example processing modules are shown separately, in one example non-limiting implementation, the processing modules 370 are stored in the memory 304; and the processing modules are collectively referred to as processing modules 370.

Still referring to FIG. 3, understood is that the system is not intended to be limited to the components shown. One or more components of the control and processing unit 300 are provided as an external component or device. In one example non-limiting implementation, the navigation engine 384 is provided as an external navigation system that is integrated with the control and processing unit 300.

Still referring to FIG. 3, some implementations are implemented using the processor 302 without additional instructions stored in memory 304. Some implementations are implemented using the instructions stored in memory 304 for execution by one or more general purpose microprocessors. Thus, the present disclosure is not limited to a specific configuration of hardware and/or software.

While some implementations may be implemented in fully functioning computers and computer systems, various implementations are capable of being distributed as a computing product in a variety of forms and are capable of being applied, regardless of the particular type of machine or computer-readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer-readable storage medium, and/or a non-transitory computer-readable storage medium, may be used to store software and data which, when executed by a data processing system, causes the system to perform various methods. The executable software and data may be stored in various places, including, for example ROM, volatile RAM, non-volatile memory, and/or cache. Portions of this software and/or data may be stored in any one of these storage devices.

Examples of computer-readable storage media include, but are not limited to, recordable and non-recordable type media, such as volatile and non-volatile memory devices, read-only memory (ROM), random-access memory (RAM), flash memory devices, floppy disks, and other removable disks, magnetic disk storage media, optical storage media, e.g., compact discs (CDs), digital versatile disks (DVDs), etc., among others. The instructions may be embodied in digital and analog communication links for electrical, optical signals, acoustical signals, and/or other forms of propagated signals, such as carrier waves, infrared signals, digital signals, and the like. The storage medium comprises the Internet cloud, storage media therein, and/or a computer-readable storage medium, and/or a non-transitory computer-readable storage medium, including, but not limited to, a disc.

At least some of the methods herein described are capable of being distributed in a computer program product comprising a computer-readable medium that bears computer-usable instructions for execution by one or more processors, to perform aspects of the methods described. The medium may be provided in various forms, such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer-useable instructions may also be in various forms, including compiled code and non-compiled code.

Referring back to FIGS. 2 and 3, according to one aspect of the present disclosure, the navigation system 200, comprising the control and processing unit 300, provides tools to a surgeon and/or a neurosurgeon that will lead to the most informed, least damaging, neurosurgical operations. In addition to removal of brain tumors and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body, such as breast biopsies, liver biopsies, etc. While several examples have been provided, aspects of the present disclosure may be applied to other suitable medical procedures.

Figure 4:
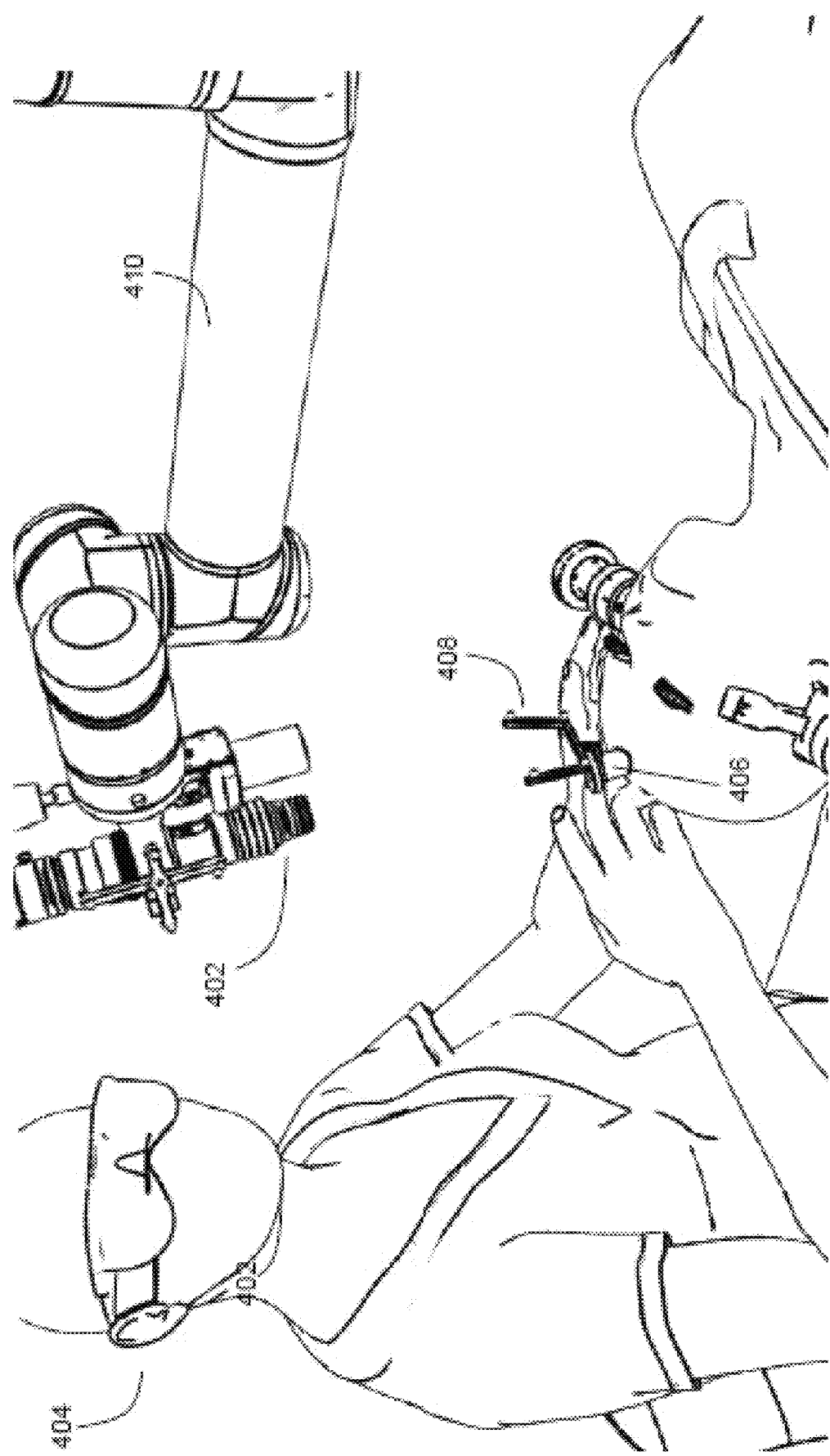
FIG. 4 is a diagram illustrating an example implementation port-based brain surgery, using a video scope, according to non-limiting implementations.

Referring to FIG. 4, this diagram illustrates a non-limiting example of a port-based brain surgery procedure using a video scope, according to non-limiting implementations of the present disclosure. An operator 404, for example a surgeon, may align a video scope 402 to peer down a port 406. The video scope 402 is attached to an adjustable mechanical arm 410. The port 406 may have a tracking tool 408 attached thereto, wherein the tracking tool 408 is tracked by a tracking camera of a navigation system.

Still referring to FIG. 4, even though the video scope 402 comprises an endoscope and/or a microscope, these devices introduce optical and ergonomic limitations when the surgical procedure is conducted over a confined space and over a prolonged period, such as the case with minimally invasive brain surgery.

Figure 5:
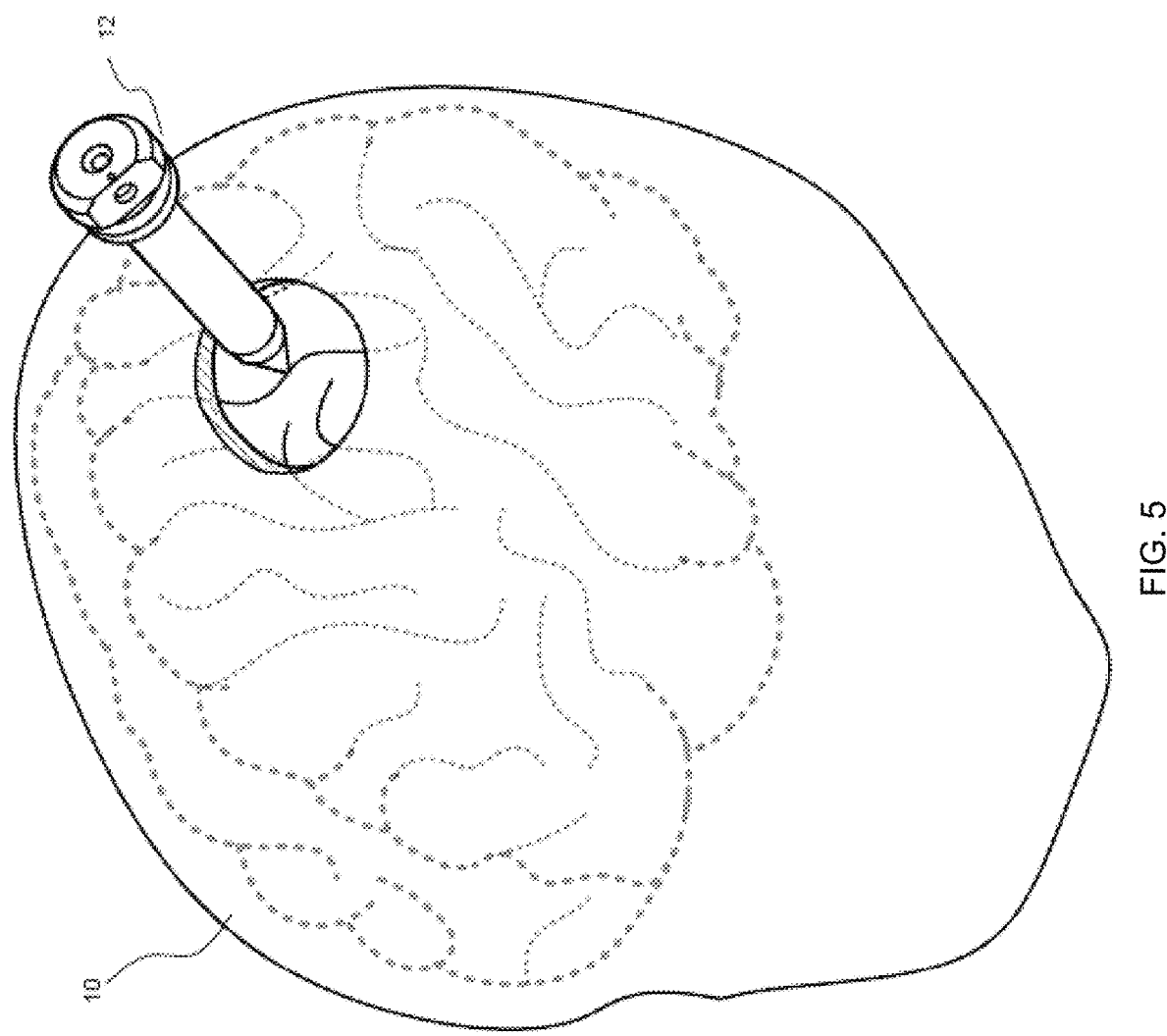
FIG. 5 is a diagram illustrating insertion of an access port into a human brain for providing access to interior brain tissue during a medical procedure, according to non-limiting implementations.

Referring to FIG. 5, this diagram illustrates the insertion of an access port 12 into a human brain 10, in order to provide access to interior brain tissue during a medical procedure, according to non-limiting implementations of the present disclosure. An access port 12 is inserted into a human brain 10, thereby providing access to interior brain tissue. The access port 12 comprises instruments, such as catheters, surgical probes, and/or cylindrical ports, e.g., the NICO® BrainPath® device. Surgical tools and instruments may then be inserted within a lumen of the access port 12 in order to perform surgical, diagnostic, or therapeutic procedures, such as resecting tumors as necessary. However, the present disclosure applies equally well to catheters, DBS needles, a biopsy procedure, and also to biopsies and/or catheters in other medical procedures performed on other parts of the body.

Still referring to FIG. 5, in the example of a port-based surgery, a straight and/or linear access port 12 is typically guided down a sulci path of the brain. Surgical instruments and/or surgical tools would then be inserted down the access port 12.

Figure 6:
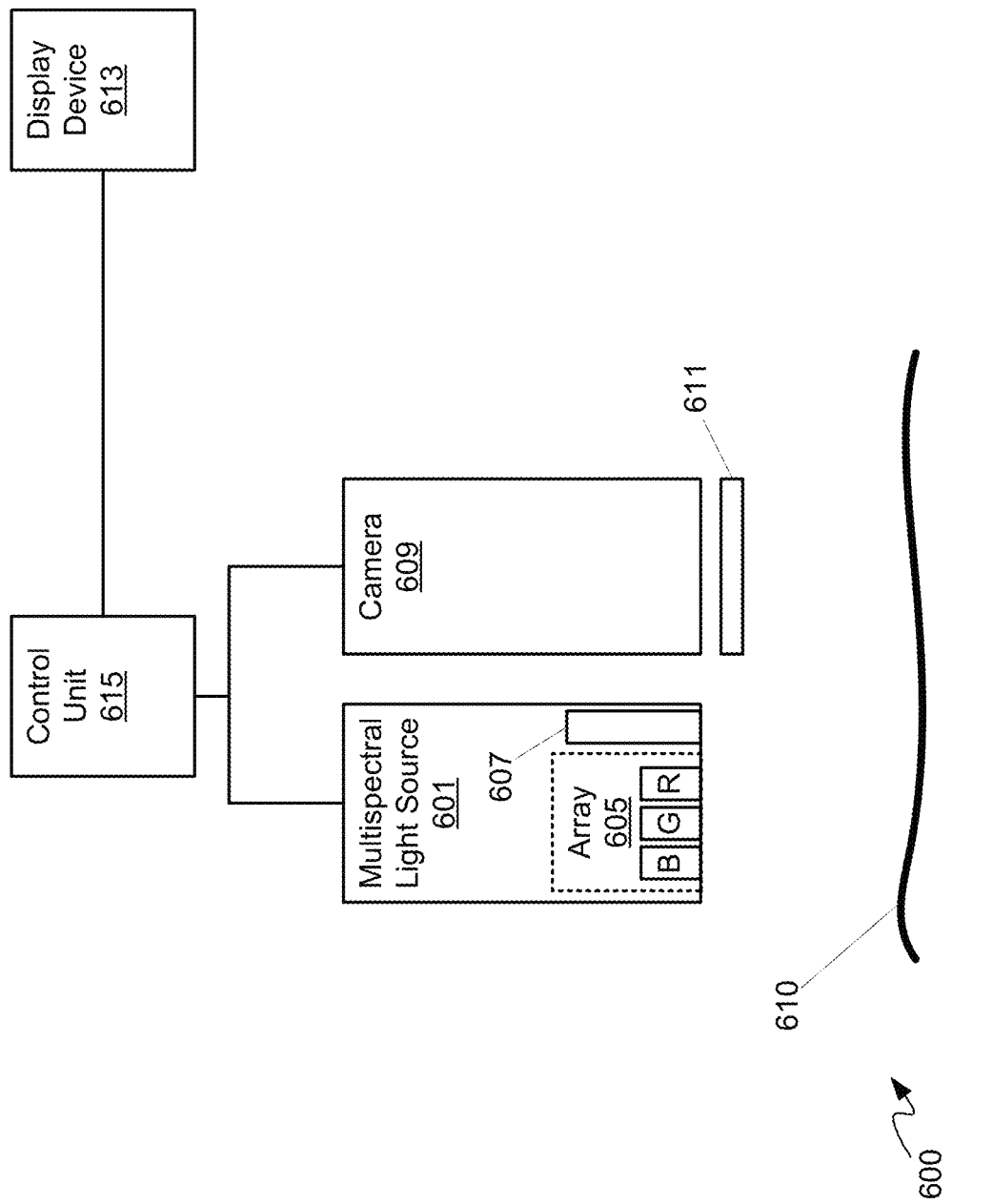
FIG. 6 is a diagram illustrating a multispectral synchronized imaging system, according to non-limiting implementations.

Referring to FIG. 6, this diagram illustrates an example of a multispectral medical imaging system 600 that could be used with access port 12, according to non-limiting implementations of the present disclosure. The system 600 comprises: a multispectral light source 601, the multispectral light source comprising a light emitting diode (LED) array 605, the LED array 605 comprising: at least one blue LED (as indicated by "B" in FIG. 6), at least one green LED (as indicated by "G" in FIG. 6), and at least one red LED (as indicated by "R" in FIG. 6); and one or more non-visible light sources 607 arranged side by side with LED array 605, each of the at least one blue LED, the at least one green LED, the at least one red LED, and the one or more non-visible light sources 607 being independently addressable such that multispectral light source 601 is configured to emit in a sequence: at least visible white light, and non-visible light in one or more given non-visible frequency ranges; a camera 609 arranged to receive light from a tissue sample 610 illuminated by multispectral light source 601 in the sequence; an optical filter 611 arranged to filter the light from tissue sample 610 received at camera 609, the optical filter configured to: transmit visible light from LED array 605; filter out non-visible light from the one or more non-visible light sources 607 in the one or more given non-visible frequency ranges; and otherwise transmit excited light emitted by tissue sample 610 under excitation by the non-visible light from the one or more non-visible light sources 607; a display device 613; and, at least one control unit 615 configured to: control multispectral light source 601 to emit the sequence; synchronize acquisition of respective images at the camera 609 for each of blue light, green light, the white light, and the excited light received at camera 609, as reflected by tissue sample 610; and, output the respective images in a respective sequence to display device 613.

For clarity, appreciated is that the terms "visible" and "non-visible," as used herein, refer to a human vision system (HVS). Hence, the term "visible light," as used herein, comprises light that is considered visible in a human vision system and/or is visible to an average human being. Similarly, the term "non-visible light," as used herein, comprises light that is considered non-visible in a human vision system and/or is non-visible to an average human being.

Referring back to FIG. 6, while not depicted, a multispectral light source 601, a camera 609, and an optical filter 611 are adapted for use with the access port 12, corridor-based surgery, and/or the like. In other words, the spectral light source 601, the camera 609, and the filter 611 can be components of an endoscope and the like, used with the access port 12, corridor-based surgery, and/or the like. Put another way, the multispectral light source 601, the camera 609, and the optical filter 611 are configured for use with a surgical port configured for corridor-based surgery, as below described in more detail with respect to FIG. 12.

Still referring to FIG. 6, the components of system 600 will now be described in detail. In particular, the multispectral light source 601, hereafter interchangeably referred as the light source 601, comprises an integrated light source, for example, that comprises an LED array 605 (hereafter interchangeably referred as the array 605) and one or more non-visible light sources 607. While only one LED is depicted for each color LED in array 605, the array 605 comprises arrays of LEDs for each color. One or more non-visible light sources 607 comprise one or more infrared (IR) diodes and/or one or more IR lasers and/or one or more ultraviolet (UV) diodes and/or one or more UV laser.

Still referring to FIG. 6, a camera 609 comprises one or more of a CCD camera, a digital camera, an optical camera, and the like. The camera 609 is generally configured to acquire digital images.

Still referring to FIG. 6, an optical filter 611, below described in more detail, comprises a dichroic filter and the like. The optical filter 611 is located at least in front of an image sensor of the camera 609 and/or in front of a lens of camera 609. Either way, light imaged by the camera 609 is generally filtered by the optical filter 611.

Still referring to FIG. 6, as described above, the optical filter 611 is configured to: transmit visible light from LED array 605; filter out non-visible light from one or more non-visible light sources 607 in the one or more given non-visible frequency ranges; and otherwise transmit excited light emitted by tissue sample 610 under excitation by the non-visible light from the one or more non-visible light sources 607; a display device 613. In other words, the optical filter 611 transmits light from LEDs in array 605, does not transmit light from one or more non-visible light sources 607, but transmits light emitted from the tissue sample 610 when excited by non-visible light from one or more non-visible light sources 607.

Still referring to FIG. 6, as such, a transmission spectrum of optical filter 611 is selected for compatibility with one or more non-visible light sources 607; and any specific imaging techniques and/or dyes to be used in the tissue sample 610 during surgery. For example, the tissue sample 610 is treated with a given dye, comprising to fluorescence dyes, that fluoresce when irradiated by non-visible light (including, but not limited to one or more of PpIX fluorophore, that fluoresces when irradiated by UV light, and ICG fluorophore, that fluoresces when irradiated by IR light). As such, in this example, a transmission spectrum of optical filter 611 is selected that transmits fluorescent light emitted by tissue sample 610, but does not transmit and/or blocks the excitation light from one or more non-visible light sources 607.

Still referring to FIG. 6, hence, in some implementations, one or more non-visible light sources 607 comprises an ultraviolet (UV) LED, and the like, and optical filter 611 is configured to filter out UV light from the UV LED, and transmit the excited light emitted by tissue sample 610 under excitation from the UV LED.

Still referring to FIG. 6, alternatively, in other implementations, one or more non-visible light sources 607 comprises an infrared (IR) laser, and the like, and optical filter 611 is configured to filter out IR light from the IR laser, and transmit the excited light emitted by tissue sample 610 under excitation from the IR laser.

Still referring to FIG. 6, however, in other implementations, one or more non-visible light sources 607 can comprise both a UV light source and an IR light source, and optical filter 611 is adapted accordingly to block light from both.

Figure 7:
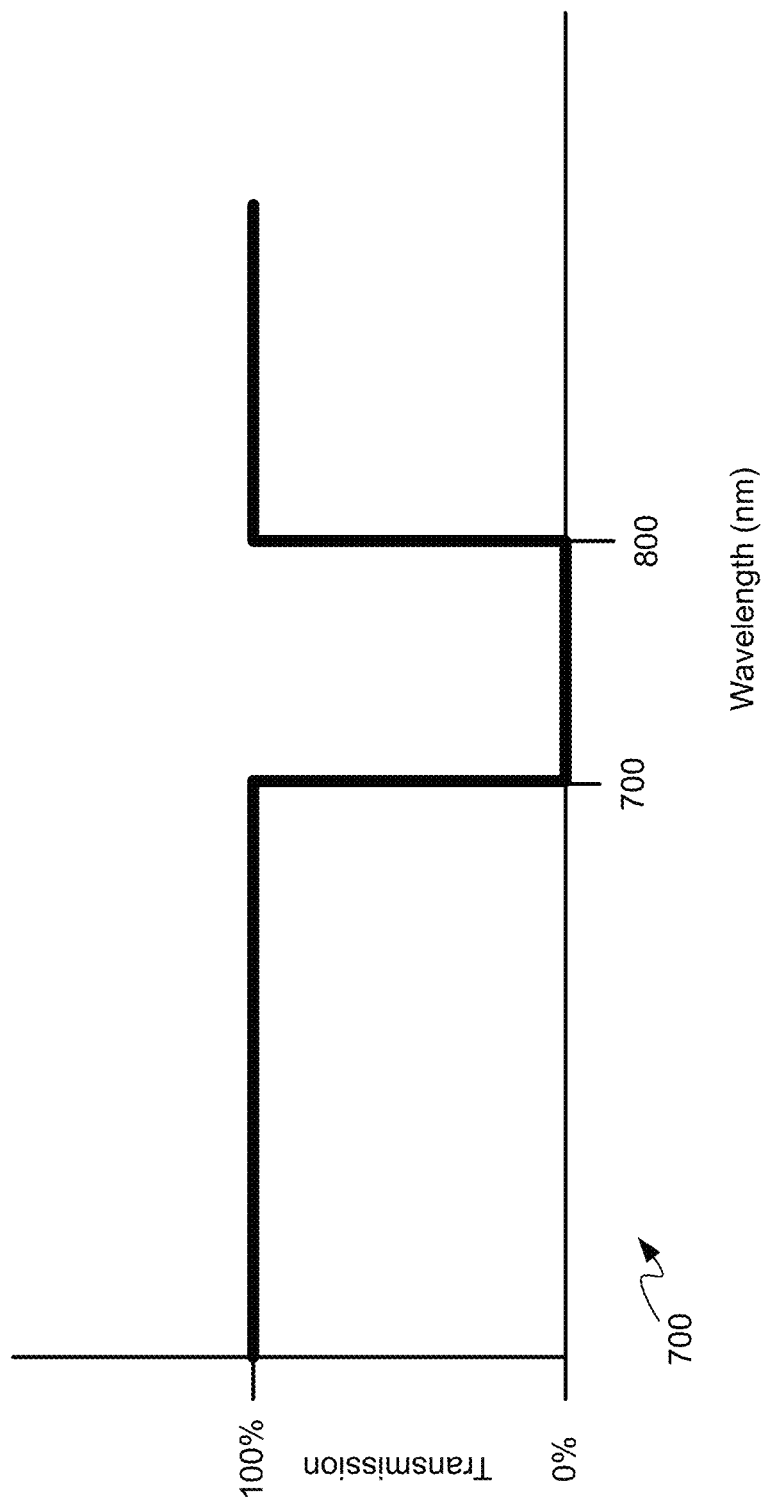
FIG. 7 is a diagram illustrating an example transmission spectrum of an optical filter in the multispectral synchronized imaging system, as shown in FIG. 6, according to non-limiting implementations.

Referring to FIG. 7, this diagram illustrates a non-limiting transmission spectrum 700 of optical filter 611, assuming that one or more non-visible light sources 607 comprises an infrared (IR) laser, and the like, and optical filter 611 is configured to filter out IR light from the IR laser, and transmit the excited light emitted by tissue sample 610 under excitation from the IR laser, according to non-limiting implementations of the present disclosure. Specifically, assumed is that the IR laser emits light in a range of approximately 700 nm to approximately 800 nm and that the tissue sample 610 emits light above approximately 800 nm when irradiated by light from the IR laser. Hence, in the range of approximately 700 nm to approximately 800 nm, light is not transmitted by the optical filter 611, e.g. transmission is approximately 0%, but outside of the range of approximately 700 nm to approximately 800 nm, light is transmitted, e.g. transmission is approximately 100%. Hence, in these implementations, the camera 609 can image light in the visible range below 700 nm from LED array 605 that is reflected to the camera 609 by the tissue sample 610; and the camera 609 can also image light emitted by the tissue sample 610 when excited by light from the one or more non-visible light sources 607.

Still referring to FIG. 7, while a specific range of wavelengths, where the light is not transmitted, is depicted, in other implementations, other ranges of wavelengths are selected that are compatible with light emitted from the one or more non-visible light sources 607. Furthermore, while not depicted, the optical filter 611 is further configured to block transmission of light below a visible range of wavelengths and/or in a UV range of wavelengths, and/or configured to block transmission of light above a given wavelength, e.g. above 900 nm, or 1000 nm and/or in the far infrared, to ensure that far IR light does not interfere with operation of system 600.

Referring back to FIG. 6, a display device 613 comprises any suitable display device, including, but not limited to, cathode ray tubes, flat panel displays, and the like. For example, the display device 613 comprises one or more of monitors 205, 211, as depicted in FIG. 2, and/or displays 305, 311, as depicted in FIG. 3.

Still referring back to FIG. 6, at least one control unit 615 is generally configured to control the light source 601 and the display device 613 and to receive images from camera 609. Hence, the at least one control unit 615 is interconnected with each of the light source 601, the camera 609 and the display device 613. In some implementations, the at least one control unit 615 comprises the control and processing unit 300, as depicted in FIG. 3, and/or is in communication with the control and processing unit 300, as depicted in FIG. 3.

Still referring back to FIG. 6, the at least one control unit 615 further comprises any suitable combination of computing devices, processors, memory devices, and the like. In particular, the at least one control unit 615 comprise one or more of a data acquisition unit, configured to acquire data and/or images at least from camera 609, and an image processing unit, configured to process data and/or images from camera 609 for rendering at display device 613.

Still referring back to FIG. 6, in particular, the at least one control unit 615 controls the multispectral light source 601 to emit light in a sequence that comprises visible white light, e.g. from the array 605, and non-visible light, e.g., from one or more non-visible light sources 607. Hence, the at least one control unit 615 causes the tissue sample 610 to be irradiated with at least white light and non-visible light in a sequence, e.g., see FIG. 8. The sequence can also include blue light, emitted from the blue LED, and green light, emitted from the green LED.

Still referring back to FIG. 6, the tissue sample 610 reflects the white light (and blue light and green light) into the camera 609 through the optical filter 611, and emits excited light under excitation from the non-visible light from the one or more non-visible light sources 607, which is also received at the camera 609 through the optical filter 611 (which also removes the non-visible light from one or more non-visible light sources 607). Hence, the camera 609, alternately (and/or in a sequence), produces optical images of the tissue sample 610, when irradiated with white light, blue light, and green light, and images of the excited light emitted by the tissue sample 610.

Still referring back to FIG. 6, hence, the at least one control unit 615 is also configured to synchronize acquisition of respective images at the camera 609 for each of the blue light, the green light, the white light, and the excited light received at camera 609, as reflected and/or emitted by tissue sample 610. For example, the at least one control unit 615 tracks when the multispectral light source 601 is emitting a particular color and/or type of light, e.g., green, blue, white, non-visible, and simultaneously classifies an image received from the camera 609 with such emission as being generated using the particular color and/or type of light. Hence, the at least one control unit 615 coordinates emission of light from the multispectral light source 601 with acquisition of images produced by the light at the camera 609.

Still referring back to FIG. 6, respective images, that result from each particular color and/or type of light, is output in a respective sequence to the display device 613 for thereupon rendering. Such images can, for example, assist a surgeon with guiding surgical tools in an access port during corridor-based surgery. For example, images, produced using visible light, is used for an optical view of the tissue sample 610, while images, produced from excited light from the tissue sample 610, is used for fluorescence guided surgery. Indeed, using the system 600, a surgeon can switch back and forth between white light guided surgery (and/or surgery using blue light and/or green light) and fluorescence guided surgery.

Still referring back to FIG. 6, indeed, various sequence of light used to irradiate the tissue sample 610 are within the scope of present implementations. For example, the sequence can comprise the visible white light, and the non-visible light alternating. Alternatively, the sequence can comprise visible white light, green light, blue light, and the non-visible light, alternating. However, the sequence can also comprise: one or more of a user-configured sequence; and simultaneous emission of light from two or more of the at least one blue LED, the at least one green LED, the at least one red LED. Indeed, any sequence that will assist a surgeon view tissue sample 610 using images rendered at the display device 613 is within the scope of present implementations.

Still referring back to FIG. 6, in some implementations, the at least one control unit 615 further control intensity of LEDs in the array 605. For example, respective relative intensity of each of the at least one blue LED, the at least one green LED, the at least one red LED is adjusted to change one or more of color temperature of the visible white light and color rendering of respective images output to the display device 613. For example, color quality of light and/or white light is described by two parameters: correlated color temperature (CCT) and color rendering index (CRI), and by respective relative intensity of each of the at least one blue LED, the at least one green LED, the at least one red LED, a given and/or desired CCT and CRI can provided to, in turn, achieve a given color appearance of tissue sample 610, including a CCT and CRI within desired ranges, e.g., for a "good" color appearance.

Figure 8:
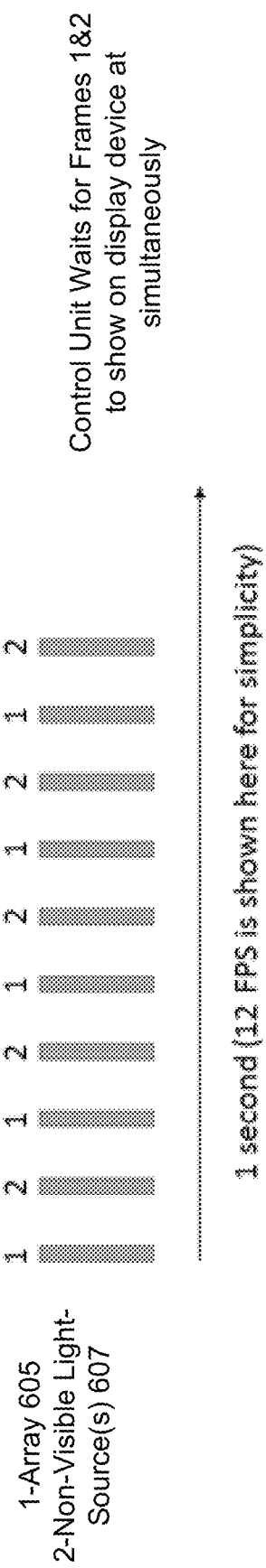
FIG. 8 is a diagram illustrating a light emission sequence of a multispectral light source of the multispectral synchronized imaging system, as shown in FIG. 6, according to non-limiting implementations.

Referring to FIG. 8, in any event, this diagram illustrates a sample sequence that is implemented at the multispectral light source 601 in which light from the array ("1") 605 alternates with non-visible light ("2") from the one or more non-visible light sources 607, according to non-limiting implementations of the present disclosure. In particular, the sequence comprises the visible white light, and the non-visible light alternating, at a rate of 12 frames per second (FPS), which is also the rate at which the corresponding images are rendered at the display device 613.

Still referring to FIG. 8, indeed, images rendered at the display device 613 is at a rate (with multispectral light source 601 controlled at a corresponding rate) where the images appear to be simultaneously rendered to a human vision system. Hence, for example, images that result from tissue sample 610 being irradiated with white light appear to be combined with images formed from excited light emitted from tissue sample 610, thereby combining white light surgery and fluorescence guided surgery, and the like; in other words, features of the tissue sample 610 that are visible only using fluorescence-guided surgery are combined at the display device 613 with features of the tissue sample 610 visible when the tissue sample 610 is irradiated with white light.

Still referring to FIG. 8, hence, the at least one control unit 615 is further configured to output the respective images in the respective sequence to display device 613. In some implementations, such images is static, for example, one or more acquired images is rendered at display device 613, statically, e.g., one or more images are acquired and rendered at the display device 613 rather than a stream of images. In other implementations, the at least one control unit 615 is further configured to output the respective images in the respective sequence to display device 613 in a video stream and/or at a rate where the respective images are simultaneously rendered to a human vision system. For example, in some implementations, such rates can include, but are not limited to, 12 FPS and higher. However, the rate of rendering images at the display device 613 can also depend on a rate at which images are acquired at camera 609. For example, if the camera acquires images at a rate of 60 Hz, an output rate of images at the display device 613 is approximately half the camera rate and/or approximately 30 Hz, assuming that two frames are captured, one visible and one-non-visible. However, other rates are within the scope of present implementations and can depend on at least one of a configuration of camera 609, a configuration of display device 613, a number of light sources in the multispectral light source 601, and a number of frames dedicated to each of the light sources in the multispectral light source 601.

Still referring to FIG. 8, indeed, the LEDs of the array 605, as well as of the one or more non-visible light sources 607 is selected based on the rate images that are to be provided at the display device 613. For example, specific LEDs types (for the array 605) and the laser diodes (for the one or more non-visible light sources 607) is selected where transient times are less than a microsecond.

Still referring to FIG. 8, similarly, wavelengths of each LED of the LEDs of the array 605 and the laser diodes for the one or more non-visible light sources 607 is selected which maximize a number of modalities that is measured in conjunction with the camera synchronization. In a particular non-limiting implementation, two types of laser diodes are used at the one or more non-visible light sources 607 that emit both UV light and IR light. In one particular non-limiting implementation, the array 605 comprises: one or more 460 nm blue LEDs, one or more 530 nm green LEDs; and one or more 620 nm red LEDs; and the non-visible light sources 607 comprise: one or more 415 nm UV LEDs, and one or more 785 nm IR laser diodes. As such, a transmission spectrum of the optical filter 611 is adapted to transmit light in the range if the LEDs of the array 605, and to block light emitted by both the one or more 415 nm UV LEDs, and the one or more 785 nm IR laser diodes.

Still referring to FIG. 8, use of such LEDs, UV LEDs and IR laser diodes can enable several modes and/or use cases in system 600 which can include, but is not limited to: UV LED: excitation of PpIX fluorophore for better tumor margin delineation, e.g., to produce excited light from a tissue sample; Blue/Green/Red LEDs: trichromatic white light with tunable CRI (color rendering index); Blue/Green interleaved: quantitative measure of blood oxygenation and volume, i.e., the sequence can include blue and green light; diffused IR laser: excitation of ICG fluorophore for angiography, e.g., to produce excited light from a tissue sample; and speckled IR laser: quantitative measure of the blood flow.

Still referring to FIG. 8, in the last use case, the system 600 is modified to include at least a second optical filter that is exchanged for optical filter 611, the second optical filter and optical filer 611 being exchangeable, depending on the operating mode.

Figure 9:
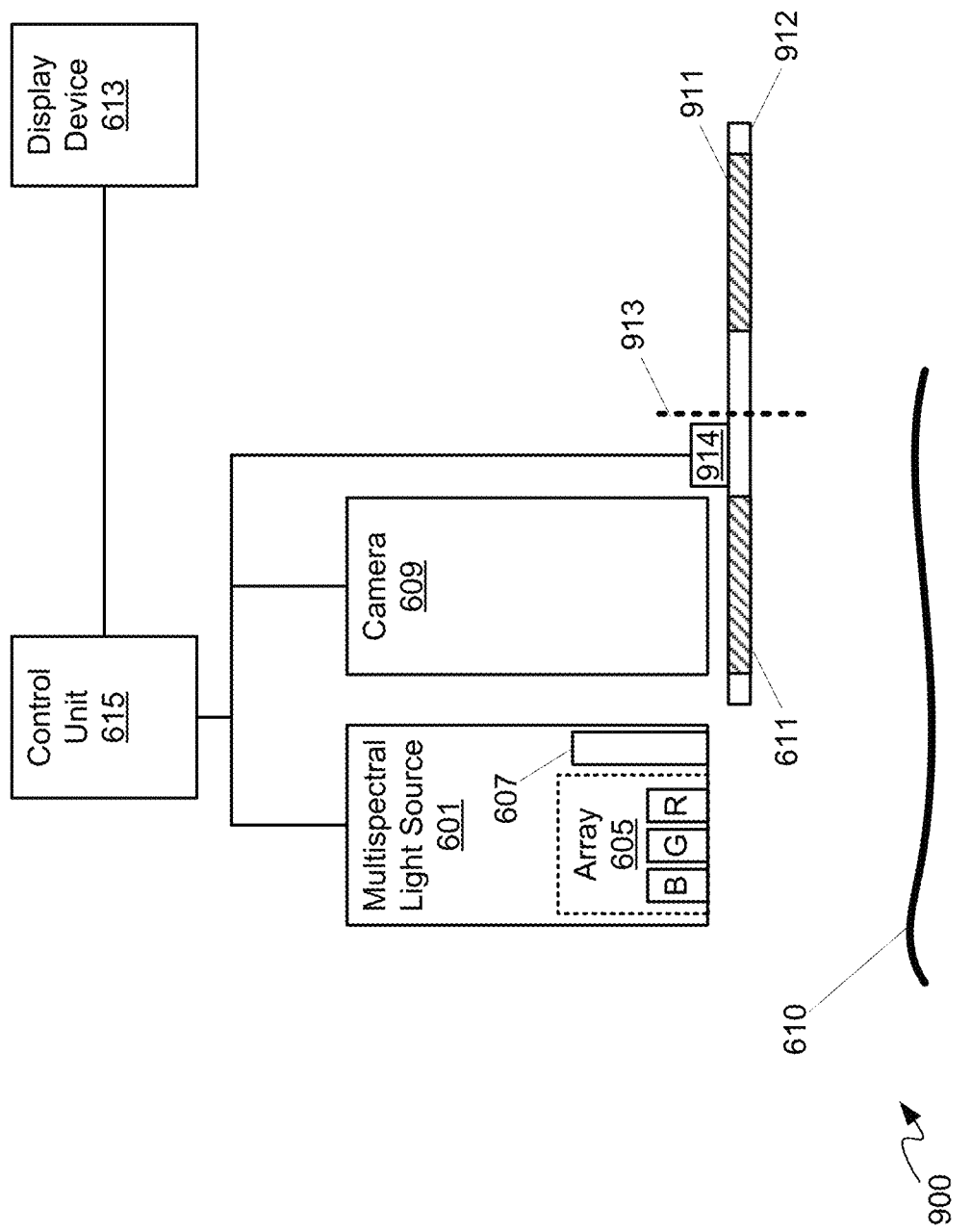
FIG. 9 is a diagram illustrating a multispectral synchronized imaging system adapted for use with multiple optical filters, according to non-limiting implementations.

Referring to FIG. 9, for example, this diagram illustrates a system 900 and is substantially similar to the system 600, with like elements having like numbers, according to non-limiting implementations of the present disclosure. However, in the system 900, the one or more non-visible light sources 607 specifically comprise an infrared (IR) laser. The system 900 further comprises a second optical filter 911, that is exchanged for the optical filter 611 under control by at least one control unit 615, the second optical filter 911 configured to transmit light from the IR laser.

Still referring to FIG. 9, for example, the optical filters 611, 911 are mounted in a filter wheel 912 configured to rotate about an axis 913. In other words, FIG. 9 depicts a cross-sectional view of the filter wheel 912. Furthermore, the filter wheel 912 further comprises an apparatus 914 configured to control a position of the optical filters 611, 911 with respect to camera 609, the apparatus 914 in communication with the at least one control unit 615. For example, the apparatus 914 comprises a stepper motor and the like. Alternatively, the optical filters 611, 911 are mounted to a slidable arm, and the like, configured to exchange the optical filters 611, 911 under control by the at least one control unit 615. Indeed, any device for exchanging the optical filters 611, 911 under control by the at least one control unit 615 is within the scope of present implementations, assuming that such devices are compatible with the surgical techniques to be used with the system 900.

Figure 10:
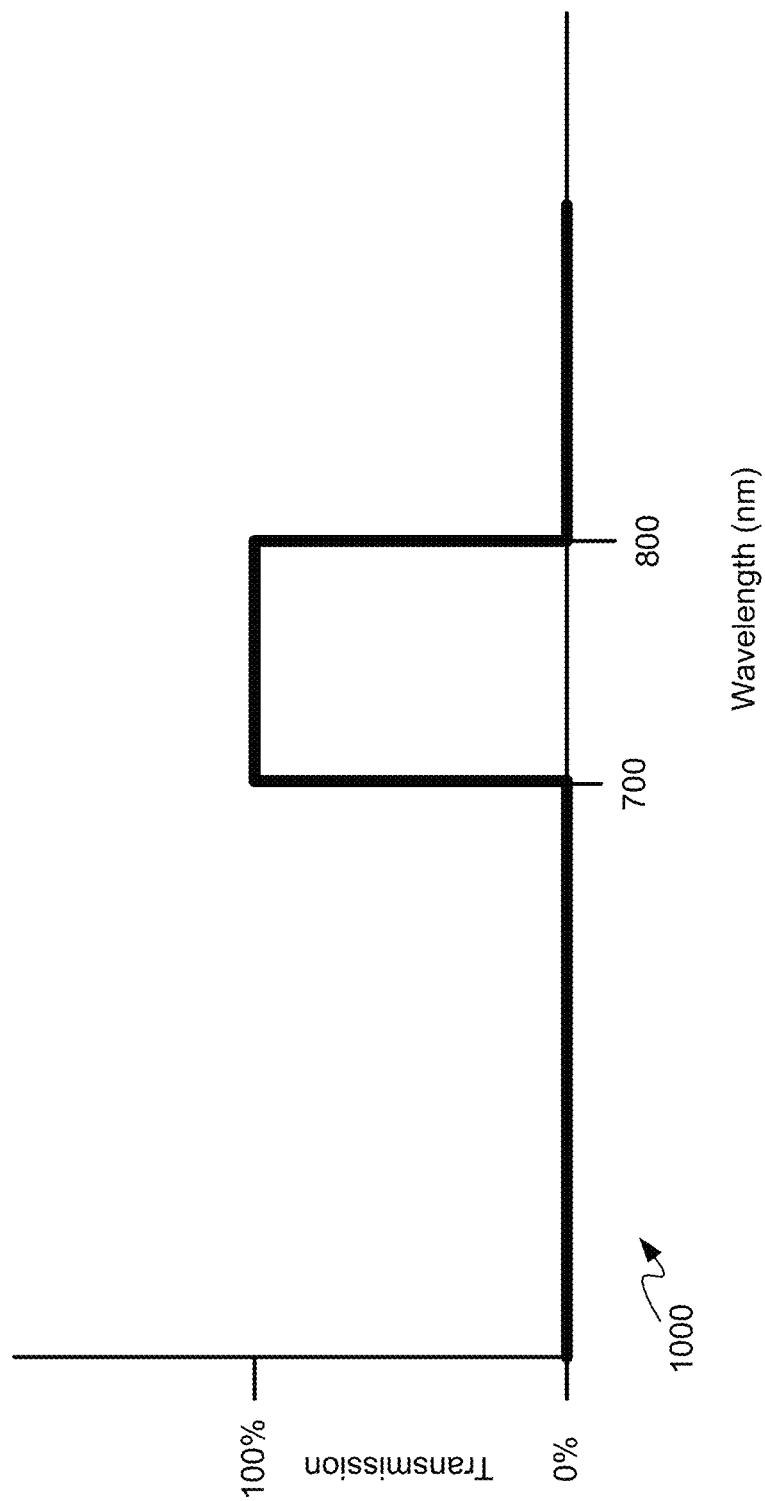
FIG. 10 is a diagram illustrating an example transmission spectrum a filter of a plurality of optical filters in the multispectral synchronized imaging system, as shown in FIG. 9, according to non-limiting implementations.

Referring to FIG. 10, this diagram illustrates a transmission spectrum 1000 of the optical filter 911, according to non-limiting implementations of the present disclosure. In contrast to the transmission spectrum 700 of the optical filter 611, as shown in FIG. 7, the transmission spectrum 1000 of the optical filter 911 transmits light from IR laser of one or more non-visible light sources 607 in a range of approximately 700 nm to approximately 800 nm and does not transmit light outside this range.

Still referring to FIG. 10, hence, the optical filter 611 is used to the operate system 900 in a manner similar to the system 600 as above described. However, the optical filter 911 is exchanged for the optical filter 611; and the IR laser of the one or more non-visible light sources 607 is operated in a speckled mode which is used to quantitatively measure blood flow in the tissue sample 610.

Still referring to FIG. 10, hence, the system 900 and/or the IR laser of one or more non-visible light sources 607, is operated in at least two modes. In particular, the IR laser is operated in one of a diffused mode, when optical filter 611 is filtering light to camera 609, and a speckled mode when second optical filter 911 is filtering light to camera 609. In other words, the diffuse mode is used when the operating system 900 in a manner similar to the system 600.

Still referring to FIG. 10, in yet further implementations, the system 900 is used in a third mode. In particular, the IR laser is operated in a speckled mode when the second optical filter 911 is filtering light to the camera 609; and the sequence of light emitted by the multispectral light source 601 comprises green light emitted from the green LED, and blue light emitted from the blue LED, when optical filter 611 is filtering light to camera 609, speckled laser light from the IR laser in the speckled mode, the green light and the blue light used for functional imaging of blood flow in the tissue sample. In other words, in the third mode, when the optical filter 611 is filtering light to the camera 609, green light and blue light is used in sequence to irradiate the tissue sample 610. Then, the optical filters 611, 911 are exchanged; and the IR laser is operated in a speckled mode (though the specific sequence of colors irradiating the tissue sample 610 is generally irrelevant, presuming the at least one control unit 615 is synchronizing such irradiation with filter position, and image acquisition).

Still referring to FIG. 10, in yet further implementations, one or more of the systems 600, 900 is adapted to include further optical filters and further light sources. For example, in some implementations, the filter wheel 912 is adapted to include three optical filters having the following transmission characteristics: Filter 1: Transmits light in a visible range of approximately 400 nm to approximately 700 nm, allowing visible light reflected from tissue sample 610 to be imaged by camera 609, and which is used for "standard" white light surgery; Filter 2: Transmits light in an extended range of approximately 400 nm to approximately 800 nm, allowing light from an IR laser operated in a speckled mode to be imaged by camera 609, and which is used for concurrent white light surgery and quantitative blood physiology measurement; and Filter 3: Transmits light in a fluorescent range of approximately 430 nm to approximately 700 nm, and from approximately 820 nm to approximately 860 nm, which blocks light from both UV and IR light sources while allowing light from the emission of PpIX & ICG from tissue sample 610 to be imaged by camera 609.

Still referring to FIG. 10, in other words, optical filters respective to light emitted from multispectral light source 601 is used depending on a mode of operation of the system and what wavelengths of light are being reflected and/or emitted by tissue sample 610. Appreciated is that yet more alternative implementations and modifications are possible.

Referring to FIG. 11, this diagram illustrates a system 1100 that is substantially similar to system 600, with like elements having like numbers, according to non-limiting implementations of the present disclosure. However, the system 1100 further comprises: a second camera 1109 arranged relative to the camera 609 to acquire three-dimensional images of the tissue sample 610. Hence, as depicted, the cameras 609, 1109 are angled and/or positioned to image a same region of the tissue sample 610. The system 1100 further comprises a second optical filter 1111, positioned to filter light into the second camera 1109, the second optical filter 1111 configured to: transmit visible light from the LED array 605 and transmit non-visible light from one or more non-visible light sources 607 in the one or more given non-visible frequency ranges. For example, the second optical filter 1111 is configured to transmit light in a fluorescent range of approximately 430 nm to approximately 700 nm, and from approximately 820 nm to approximately 860 nm, which blocks light from both UV and IR light sources while allowing light from the emission of PpIX and ICG from the tissue sample 610 to be imaged by the camera 1109; such implementations assume that the one or more non-visible light sources 607 comprises an IR laser, which is operable in one of a diffused mode and a speckled mode, and a UV laser.

Still referring to FIG. 11, hence, using two sets of cameras and respective optical filters, different modes of imaging tissue sample 610 is simultaneously performed. Alternatively, the camera 609 and the second camera 1109 is configured to capture images independent of one another, such that the system 1100 is operated in different modes at different times.

Appreciated is that there are yet more alternative implementations and modifications possible. For example, in some implementations, one or more of the system 600, 900, 1100 further comprises a thermal camera arranged to receive light from tissue sample 610 illuminated by the multispectral light source 601 in the sequence, thereby performing thermal imaging of tissue sample 610. For example, in the system 100, the camera 1109 comprises a thermal imaging camera and an optical filter 1111 that can either be removed from system 1100 or adapted to transmit light in a thermal imaging range. Furthermore, in some implementations, light sources, filters, and cameras are packaged together in an apparatus compatible for use with an access port, such as access port 12.

Referring to FIG. 12, this diagram illustrates a system 600, in which the multispectral light source 601, the camera 609, and the optical filter 611 are assumed to be packaged in an apparatus 1250, which can comprise an endoscope, and the like; as depicted, the apparatus 1250 has been inserted through the access port 12, depicted in cross-section, according to non-limiting implementations of the present disclosure.

Still referring to FIG. 12, as depicted, the apparatus 1250 comprises an optional tracking device 1255 attached to a proximal end apparatus 1250. In other words, as depicted, the system 600 optionally comprises the tracking device 1255 configured to be tracked by a navigation system. The tracking device 1255 is generally configured to be tracked by a navigation system external to the system 600, for example, a navigation system that is part of a surgical system, such as shown in FIGS. 1 to 4. While not depicted, the apparatus 1250 can further comprise a mount configured to removably attach the tracking device 1255 at a proximal end thereof, e.g., an end that is away from tissue being imaged. The tracking device 1255 is generally positioned so that a camera, and the like, of a surgical navigation system may track a position of the tracking device 1255 and, hence, a relative position of a distal end of the apparatus 1250, e.g., an end of apparatus 1250 closest to tissue sample 610. As depicted, the tracking device 1255 comprises four reflective spheres arranged in a configuration where each sphere is located at about a corner of a square. However, other numbers of spheres and other configurations are within the scope of present implementations. In particular, one or more of a number, arrangement, and configuration of such spheres are selected to provide a given tracking accuracy, including, but not limited to, a tracking accuracy that is less than approximately half a diameter of a sensing array surface. However, the tracking device 1255 comprises tracking devices other than reflective spheres. For example, in some implementations, the tracking device 1255 comprises a flexible sheath configured to measure tip position deflection, for example, deflection of a tip of the flexible sheath. Furthermore, the system 600 is adapted to include one or more tracking devices.

Still referring to FIG. 12, furthermore, the at least one control unit 615 comprises one or more ports configured for communicate with one or more of: surgical navigation system; external computing devices; electronic surgical devices; trackers; and infrared trackers.

Still referring to FIG. 12, appreciated is that yet more alternative implementations and modifications are possible. For example, at least one control unit 615 is configured to implement various image processing algorithms including, but not limited to: amplification of the color dynamics around the edge of the tumor margin under FGS mode, image fusion between WLS and FGS modes, division of the light reflectance under blue light to that of green light for blood oxygenation and volume computations, spatial computation under speckled laser illumination for blood perfusion.

Still referring to FIG. 12, when using two cameras, which is used for combined three-dimensional vision, as in system 1100, image processing algorithms implemented by at least one control unit 615 can further include finding parameters to warp image from each camera onto another. In some of these implementations, at least one control unit 615 can control multispectral light source 601 to intermittently flash blue light from the blue LED into one camera and flash blue light from the blue LED into the other camera, e.g., assuming that at least one control unit 615 is synchronizing images from the cameras, to obtain a quantitative blood physiology while warping and merging images from each camera into a single image.

Still referring to FIG. 12, in yet further implementations, systems herein described is adapted to include external sources and at least one control unit 615 can either comprise or be a component of other surgical systems and/or be in communication with a main control hub of surgical system. In such implementations, at given intervals, e.g., every second, such a main control hub cause camera acquisition of systems herein described to stop such that external source is used to perform other imaging techniques, including, but not limited to, intraoperative Raman spectroscopy. Furthermore, when tracking devices are used with systems herein described, e.g., as depicted in FIG. 12, and such tracking devices are tracked using light in an infrared spectrum such infrared light can introduce artefacts from pulsing infrared diodes on the acquired images unless optical filters herein described are further adapted to filter out such artefacts. For example, the sequence, as depicted in FIG. 8, could be modified to include an infrared tracking pulse in the 700 nm to 800 nm region between frames and/or within a frame that illuminates apparatus 1255, which is detected by a tracking system, but images of apparatus 1255 and/or the tracking pulse, is filtered out of camera 609 using optical filter 611, e.g., see FIG. 7. Hence, by using the system 600, infrared tracking is used in conjunction with FGS without introducing artefacts into images of the tissue sample 610 rendered at the display device 613 from the camera 609.

Still referring to FIG. 12, in yet further implementations, the at least one control device 615 is adapted to perform sub-frame synchronization, for example, by controlling camera shutter speeds and/or camera "sync" pulses to stagger image acquisition on a sub-frame basis; such a feature can obviate reductions in frame rate in a global acquisition of images, for example, in different spectral and/or wavelength ranges. Such a feature can also be referred to as "time multiplexing of image acquisition and illumination," which is used for different modalities of the systems 600, 900, 1100 that include a plurality of cameras that can acquire images in different spectral and/or wavelength ranges. For example, the systems 600, 900, 1100 is used as a kind of "global image and illumination scheduler" using the mentioned sync pulses, and the like, which can ensure that the various image acquisitions in the different spectral and/or wavelength ranges, e.g. tracking, visible, non-visible, etc., do not interfere with each other as they all require different lighting and capture environments. For example, in a specific non-limiting example, such sub-frame synchronization could be implemented in a system comprising multiple cameras, each with a frame rate of 60 Hz; hence, a fame is acquired every $\frac{1}{60}$ of a second (however, camera speeds are often faster, and such acquisitions can occur at rates on the order of every $\frac{1}{250}$ of a second to every $\frac{1}{1000}$ of a second, and faster); in such implementations, image capture times of each camera is slightly off-set with respect to one another, and images from each camera is acquired within the $\frac{1}{60}$th of a second, within different spectral and/or wavelength ranges, and hence multispectral image is acquired without reducing frame rate.

The specific embodiments described above have been shown by way of example, and understood is that these embodiments may be susceptible to various modifications and alternative forms. Understood is that the claims are not intended to be limited to the particular forms disclosed, but rather to cover all modifications, equivalents, and alternatives falling within the spirit and scope of this disclosure.

What is claimed:

1. A multispectral synchronized imaging system, the system comprising:
   a control unit configured to:
   control a multispectral light source to emit, in a sequence, at least one of visible white light, non-visible light, and to emit, simultaneously, at least two of blue light by at least one blue LED, green light by at least one green LED, and red light by at least one red LED;
   control the multispectral light source, a filter positioning device, and a first camera in a synchronized alternating manner to acquire at least one first image and at least one second image,
   respectively output the at least one first image and the at least one second image to the display device;
   enable the multispectral light source to operate in a first mode, whereby diffused non-visible light is emitted;
   control the filter positioning device to position the first optical filter, as the selected optical filter, relative to the first camera so as to filter the diffused non-visible light from the first camera while acquiring the at least one first image, whereby the at least one first image from the first camera comprises at least one fluorescence-imaging image;
   output the at least one fluorescence-imaging image to the display device;
   enable the multispectral light source to operate in a second mode, whereby coherent non-visible light is emitted;
   control the filter positioning device to position the second optical filter, as the selected optical filter, relative to the first camera so as to transmit the coherent non-visible light to the first camera while acquiring the at least one second image, whereby the at least one second image comprises functional imaging of blood flow in the tissue;
   process the at least one first image and the at least one second image to quantitatively measure blood flow in the tissue sample; and output the at least one first image and the at least one second image to the display device along with at least one quantitative measurement of the blood flow;

wherein the at least one first image is acquired by the first camera for each illumination of tissue by the multispectral light source with the blue light, the green light, the visible white light, and the non-visible light, while a first optical filter, as a selected optical filter, is positioned by the filter positioning device relative to the first camera, and wherein the at least one second image is acquired for illumination of the tissue by the multispectral light source with the non-visible light, while a second optical filter, as the selected optical filter, is positioned by the filter positioning device relative to the first camera.

2. The multispectral synchronized imaging system of claim 1, further comprising:

the multispectral light source configured to illuminate the tissue, the multispectral light source comprising:

a light emitting diode (LED) array configured to emit visible light, the visible light comprising white light, the LED array comprising: the at least one blue LED configured to emit the blue light, the at least one green LED configured to emit the green light, and the at least one red LED configured to emit the red light, each of the at least one blue LED, the at least one green LED, and the at least one red LED being individually addressable; and at least one non-visible light source configured to emit the non-visible light in at least one non-visible frequency range, the at least one light source comprising an infrared (IR) laser, the at least one light source arranged side by side with the LED array and is independently addressable, the at least one non-visible frequency range comprising an IR frequency range, and the non-visible light comprising non-visible light emitted from the IR laser;

the first camera arranged to capture the at least one first image of the tissue by receiving the light being one of reflected from, and emitted from, the tissue;

the first optical filter and the second optical filter;

the filter positioning device configured to selectively position the selected one optical filter of the first optical filter and the second optical filter relative to the first camera, the selected one optical filter positioned relative to the first camera, and the light being one of reflected from, and emitted from, the tissue prior to being received by the first camera, wherein, when the first optical filter, as the selected one optical filter, is positioned by the filter positioning device relative to the first camera and the visible white light from the LED array, illuminating the tissue, is reflected from the tissue, the first optical filter is configured to transmit the reflected visible white light to the first camera, wherein, when the first optical filter, as the selected one optical filter, is positioned by the filter positioning device relative to the first camera and the non-visible white light from the at least one non-visible light source in the at least one non-visible frequency range, illuminating the tissue, reflects from the tissue and excites the tissue to emit a first tissue-emitted light, the first optical filter is configured to filter the reflected non-visible white light so as to be blocked by being received by the first camera and transmit the first tissue-emitted light to the first camera, wherein, when the first optical filter, as the selected one optical filter, is positioned by the filter positioning device relative to the first camera and the non-visible light from the IR laser, illuminating the tissue, reflects from the tissue and excites the tissue to emit a second tissue-emitted light, the first optical filter is configured to filter the reflected non-visible light so as to be blocked by being received by the first camera and transmit the second tissue-emitted light to the first camera, and wherein, when the second optical filter, as the selected one optical filter, is positioned by the filter positioning device relative to the first camera and the non-visible light from the IR laser, illuminating the tissue, reflects from the tissue, the second optical filter is configured to transmit the reflected non-visible light to the first camera; and the display device;

wherein the at least one non-visible light source further comprises an ultraviolet (UV) light source, and wherein the first optical filter is further configured to:

transmit light in a range of approximately 430 nm to approximately 700 nm, and from approximately 820 nm to approximately 860 nm to allow light from fluorescent emission of at least one or of Protoporphyrin IX and Indocyanine green administered to the tissue to be imaged by the first camera; and block both UV light, emitted from the UV light source and reflected from the tissue, and the non-visible light, emitted from the IR laser and reflected from the tissue, from entering the first camera.

3. The multispectral synchronized imaging system of claim 2, wherein the control unit is further configured to:

control the filter positioning device to position the first optical filter, as the selected optical filter, relative to the first camera so as to filter the reflected non-visible light from being received by the first camera;

control the at least one green LED and the blue LED to respectively emit, in sequence, the green light and the blue light;

control the first camera to acquire the at least one first image of the tissue under illumination by the green light and the blue light; and process the first images to determine tissue oxygenation of the tissue sample.

4. The multispectral synchronized imaging system of claim 2, wherein the sequence further comprises alternatingly emitting the visible white light and the non-visible light.

5. The multispectral synchronized imaging system of claim 2, wherein the sequence further comprises alternatingly emitting the visible white light, the green light, the blue light, and the non-visible light.

6. The multispectral synchronized imaging system of claim 2, wherein the control unit is further configured to control the multispectral light source to adjust a respective relative intensity of each of the at least one blue LED, the at least one green LED, the at least one red LED to change one or more of: a color temperature of the visible white light; and a color rendering of the at least one first image and the at least one second image output to the display device.

7. The multispectral synchronized imaging system of claim 2, further comprising a second camera arranged relative to the first camera to acquire at least one three-dimensional image of the tissue, wherein the control unit is further configured to determine parameters to warp together images acquired by the first camera and with images acquired by the second camera.

8. The multispectral synchronized imaging system of claim 7, wherein the first camera and the second camera are configured to acquire images independent of one another such that one of the first camera and the second camera acquires images at times when the other of the first camera and the second camera does not acquire images and vice versa.

9. The multispectral synchronized imaging system of claim 7, wherein the control unit is further configured to control the first camera and the second camera such that image acquisition times of each of the first camera and the second camera are off-set with respect to one another such that images acquired by each of the first camera and the second camera are acquired within 1/60th of a second of each other.

10. The multispectral synchronized imaging system of claim 2, wherein the control unit is further configured to output the at least one first image and the at least one second image to the display device at a rate in a range of at least 12 frames per second.

11. The multispectral synchronized imaging system of claim 2, further comprising a thermal camera arranged to acquire images by receiving the light being at least one of reflected from, and emitted by, the tissue.

12. The multispectral synchronized imaging system of claim 11, further comprising a third optical filter disposed in relation to the thermal camera, wherein the third optical filter is configured to transmit light in a thermal imaging frequency range.

13. The multispectral synchronized imaging system of claim 2,
wherein the control unit comprises at least one port, and
wherein the control unit is further configured to communicate, via the at least one port, with at least one of: an external computing device; an electronic surgical device; a tracker; and an infrared tracker.

14. The multispectral synchronized imaging system of claim 2, wherein the multispectral light source, the first camera, and the first optical filter, the second optical filter, and the filter positioning device are packaged together for insertion through a surgical port for corridor based surgery.

15. The multispectral synchronized imaging system of claim 2, further comprising a second camera disposed and configured, in relation to the first camera, in a manner enabling one of simultaneously imaging a same region of the tissue and asynchronously imaging the same region of the tissue,
wherein the second camera is further configured to acquire at least one three-dimensional image of the tissue,
wherein the first optical filter is disposed in relation to first camera and the second optical filter is disposed in relation to the second camera, and
wherein the second optical filter further configured to:
transmit the visible light from the LED array reflected from the tissue; and
transmit the non-visible light from the at least one non-visible light source in the at least one non-visible frequency ranges reflected from the tissue, and
wherein the first camera with the first optical filer and the second camera with the second optical filter respectively enable the one of simultaneously imaging the same region of the tissue sample and asynchronously imaging the same region of the tissue in distinct imaging modes.

16. The multispectral synchronized imaging system of claim 15, wherein the multispectral light source, the first optical filter, the second optical filter, the filter positioning device, the first camera, and the second camera are one of packaged together in, and form, an endoscope compatible for use with an access port.

17. The multispectral synchronized imaging system of claim 16, further comprising at least one tracking device removably coupled with a proximal end of the endoscope, the at least one tracking device configured to be tracked by an external navigation system external to system via infrared tracking, wherein at least one of the first optical filter and the second optical filter is further configured to filter an artefact caused by using the infrared tracking.

18. The multispectral synchronized imaging system of claim 2, further comprising a second camera arranged relative to the first camera, wherein the control unit is further configured to perform at least one of:
communicate with at least one of: a surgical navigation system, an external computing device, an electronic surgical device, at least one tracker, and at least one infrared tracker;
implement at least one image processing algorithm comprising at least one of: an amplification algorithm for amplifying color dynamics around an edge of a tumor margin under a fluorescence guided surgery (FGS) mode, an image fusion algorithm for fusing imaging between a white light surgery (WLS) mode and an the FGS mode, a division algorithm for dividing light reflectance under the blue light from light reflectance under the green light for blood oxygenation computation and volume computation, a spatial computation algorithm for computing speckled laser illumination for blood perfusion, and an algorithm fir finding parameters to warp an image acquired by the first camera onto an image acquired by the second camera;
control the multispectral light source to intermittently flash the blue light from the blue LED and reflected from the tissue into one camera and flash blue light from the blue LED into the first camera to acquire a first blue light image and flash the blue light from the blue LED and reflected from the tissue into the second camera to acquire a second blue light image to obtain a quantitative blood physiology while warping and merging the first blue light image and the second blue light image into a single image; and
communicate with a main control hub of a surgical system, wherein the main control hub is configured to cause an external light source to perform Raman spectroscopy.

19. The multispectral synchronized imaging system of claim 18, wherein the control unit is further configured to control illumination by the multispectral light source and acquiring of images by the first camera and the second camera for sub-frame synchronization by controlling at least one of a camera shutter speed and a camera synchronization pulse to stagger image acquisition of the first camera and the second camera on a sub-frame basis, so as to effect time multiplexing of the image acquisition and the illumination.

20. The multispectral synchronized imaging system of claim 2, wherein at least one of the first camera and the second camera comprises an optical camera.

21. The multispectral synchronized imaging system of claim 1, wherein the non-visible light source further comprising an infrared (IR) laser, wherein the one or more given non-visible frequency ranges comprise an IR frequency range, and the non-visible light comprises IR light emitted from the IR laser.

\* \* \* \* \*